United States Patent [19]

Suh et al.

[11] 4,352,059

[45] Sep. 28, 1982

[54] DETERMINATION OF MOISTURE LEVEL IN MATERIALS

[75] Inventors: Nam P. Suh, Sudbury; Stephen D. Senturia, Boston, both of Mass.; Byung H. Kim, South San Francisco, Calif.

[73] Assignee: Massachusetts Institute of Technology, Cambridge, Mass.

[21] Appl. No.: 159,221

[22] Filed: Jun. 13, 1980

[51] Int. Cl.³ .......................................... G01R 27/26
[52] U.S. Cl. .............................. 324/61 R; 204/195 W
[58] Field of Search .............. 324/61 R, 61 P; 73/73, 73/74; 361/286; 204/195 W

[56] References Cited

U.S. PATENT DOCUMENTS

| | | | |
|---|---|---|---|
| 3,252,086 | 5/1966 | Lundstrom | 324/61 |
| 3,657,644 | 4/1972 | Beam et al. | 324/61 R |
| 3,684,952 | 8/1972 | Lundstrom | 324/61 |
| 3,778,707 | 12/1973 | Vogel | 324/61 R |
| 4,097,743 | 6/1978 | Carlson | 250/339 |
| 4,109,033 | 8/1978 | Blankenhorn | 73/73 X |

FOREIGN PATENT DOCUMENTS 2851686  6/1979  Fed. Rep. of Germany .... 324/61 R

OTHER PUBLICATIONS

Antson et al., Capacitive Moisture Detector, Sahko, 1974, pp. 11, 12.
Rushton et al., The Dielectric Properties of Nylon, The British Electrical and Allied Industries Research Association, Sep. 14, 1956, pp. 1-11.
Quadra-Beam Moisture Analyzer Instruction Manual.

*Primary Examiner*—Stanley T. Krawczewicz
*Attorney, Agent, or Firm*—Arthur A. Smith, Jr.; George W. Neuner

[57] ABSTRACT

A method for determining the moisture content of dielectric materials is described wherein a sample of the material is placed between two electrodes and an electric field is applied. An alternating frequency in the range of radio waves and lower is applied to the electrodes and the dielectric loss properties of the material are determined. The dielectric loss properties are then used to determine moisture content. In an alternate embodiment, a step voltage is applied to the electrodes and the direct current is monitored. The decrease in value of direct current during a time interval following the application of the step voltage is used to determine the moisture content.

19 Claims, 5 Drawing Figures

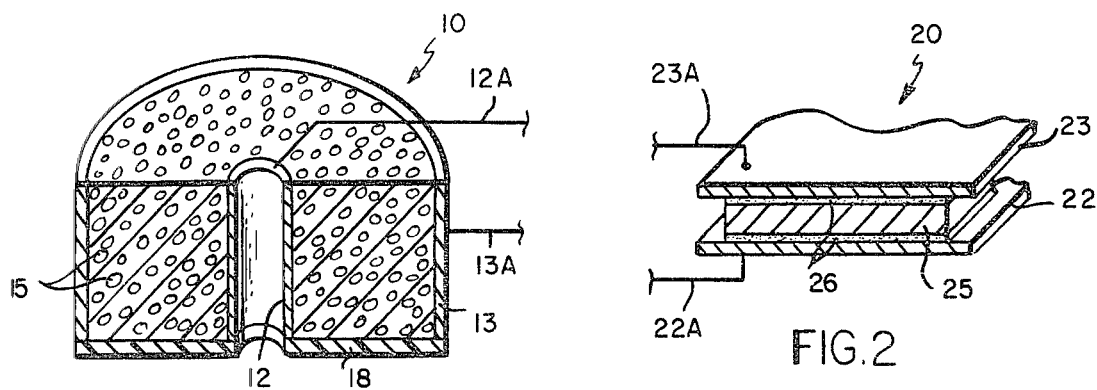
FIG.1
FIG.2
FIG.4
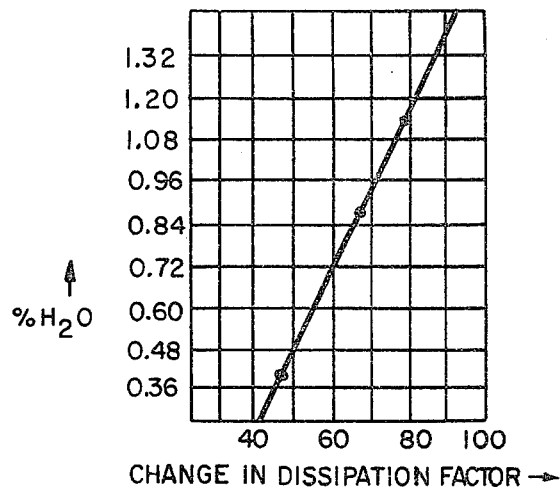
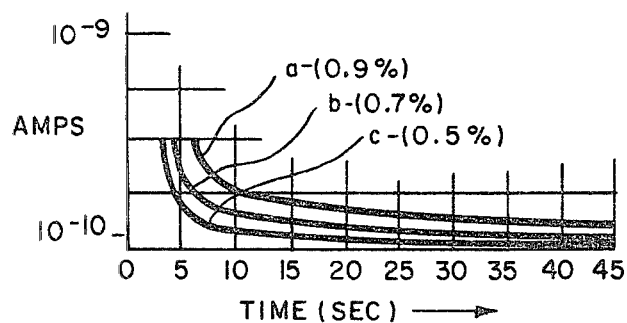
FIG.3

DETERMINATION OF MOISTURE LEVEL IN MATERIALS

FIELD OF THE INVENTION

This invention relates to methods for determining the moisture content of material and particularly to a fast and accurate method for determining the moisture content in dielectric materials such as polymers by measuring the dielectric loss factor or the loss tangent.

BACKGROUND OF THE INVENTION

The atmosphere in which physicochemical transformations are conducted is of paramount importance in many industrial operations. In particular, water vapor measured in amounts as low as a few parts per million by volume assumes important measurement focus. The presence of moisture in unwanted proportions can cause retardation of reaction. Oxidation, inhibited polymeric reaction, catastrophic freeze-ups corrosion, and impairment of catalyst activity. Moisture measurement is thus a critical need in many industries including papermaking, petroleum refining, paint manufacturing, heat treating, food production, glass manufacture, and chemical making.

In many industries the moisture content of the raw materials and products are also critical. The moisture content of materials can affect their physical properties, including mechanical strength and electrical properties, their physical appearance and their ability to be processed.

For instance, in the polymer processing industry both the processability of the polymer and the physical properties of the end product depend upon the moisture content of the granules used as raw material. The moisture content of the final product can, in some instances, markedly affect the mechanical properties such as impact strength.

Moisture content of polyolefins is an important parameter for polymer manufacturers and fabricators because water can affect the physical and appearance properties of the processed product. For example, exposure to water has been shown to cause a decrease in tensile strength of polyethylene. Similarly, since polyolefins are molded or extruded at temperatures above the boiling point of water, excessive amounts of moisture present in the raw resin can cause bubbles and streaks in the finished product. In high voltage electrical cables, polyolefin insulation materials can prematurely fail due to the presence of moisture. The moisture can lead to the development of "water trees" or low resistance leakage paths producing failure of the cable under actual use conditions.

Certan grades of thermoplastic polyester resin should be dried before injection molding in order to maintain their optimum properties. Some polyesters should not be molded unless they are adequately dried. Of course other polymers also can be benefited by drying. This is especially true when melt temperatures exceed recommended limits or when extended mold cycle times are expected. In some instances moisture levels as low as 0.02% are recommended for optimum processing.

Drying of polymers is frequently determined by the length of time that the resin is dried at a given temperature. Such drying periods can vary from a few hours to days. However, a quantitative check of the moisture level of the resin is often desirable. For such a checking technique to be useful in a mold shop it should be quick, simple and utilize inexpensive equipment.

One technique for simple moisture level determination is called the test tube/hot block technique (TTHB). It is based on the fact that moisture present in resin will vaporize when melted in a closed test tube. This moisture will condense, as it cools, in the form of tiny water droplets on the side of the glass tube. The surface area covered by this condensation on the tube can then be correlated to the moisture content of the pre-heated resin. The amount of surface area on the test tube wall covered by condensation corresponds directly to the moisture level of the resin.

Another technique is called T.V.I. after the engineer who developed it. In brief, this method entails heating a few pellets of polymer to their melting point and observing whether bubbles are present, indicating moisture in the resin, or absent, indicating a dry material.

However, both of these simple methods are primarily qualitative or semi-quantitation at best. It is readily seen that both are subject to many variables and open to considerable error if accurate moisture data is necessary.

The traditional technique for accurate analysis of moisture in polymer (ASTM Method D-789) involves a vacuum distillation followed by Karl-Fischer titration of the moisture. This method suffers from the disadvantages of being time consuming, costly in reagents and requiring a delicate laboratory technique.

A widely used method for accurate analysis of moisture in polymers is called moisture evolution analysis. The sample is heated to an operator controlled temperature in an oven to drive off any water. Moisture from the heated sample is picked up by a continuously flowing stream of externally dried nitrogen and is carried into an electrolytic cell to determine moisture content. Although relatively simple, this method still requires accurate weighing of the sample and must be conducted off line.

A method has been described for determining the moisture content of plastics, molding powders, fillers, etc. from the amplitude of the nuclear magnetic resonance (NMR) signal. Industrial NMR spectrometers for determination of moisture content have been described. However the method is still an off-line procedure and accuracy at low moisture levels of 1 to 10% may be no better than 0.5%.

The free (unbound) moisture content of many dielectric materials can be accurately measured with microwave techniques. Microwaves are strongly absorbed and scattered by water molecules because water exhibits a broadband rotational relaxation in the microwave region. Because many completely dry host materials are quite transparent in the same frequency range, a moisture-measuring technique is possible. This technique has found wide use on both a continuous process and laboratory sample basis, especially for plastic and ceramic materials. The main disadvantage of using microwave techniques for measuring moisture content is that they are not very sensitive at low moisture levels, particularly at moisture contents less than 1% where a substantial percent of the water molecules in the polymer may not be free.

Thus, it can be seen that a fast, accurate method for measuring the moisture content of dielectric materials such as polymers, particularly at low moisture levels is desired. Such a method preferably should be suitable for on-line continuous monitoring of moisture levels and capable of accepting large sample sizes.

Dielectric properties and the electrical conductivity of polymers have been widely studied by a large number of investigators. These studies were undertaken for a variety of reasons such as studying the molecular structure of a material, studying the mechanics of conduction in a material, etc. In conducting these studies it was appreciated that humidity and moisture in the material would affect the electrical properties and efforts were made to insure dryness for the studies. Several investigators have reported the effects of moisture on the electrical properties of polymers. For instance, in September 1956, Rushton and Russell, published a technical report on "The Dielectric Properties on Nylon", ERA Technology Ltd. report L/T355. In the report Rushton and Russell illustrate the variation of permittivity (E) and loss tangent (tan δ) with frequency for nylon having low moisture content and for dried nylon. However, neither Rushton and Russell nor other investigators suggested that the measurement of dielectric properties of a material at low frequencies would be useful for determining the moisture content of such materials.

SUMMARY OF THE INVENTION

We have discovered that the moisture of content of dielectric materials, particularly at low moisture levels, can be quickly and accurately determined by measuring the dielectric loss factor or loss tangent of the material at low frequency or by monitoring the decaying electrical current when a step voltage is applied to the material. We have found that the dielectric loss factor is very sensitive to the moisture level in polymers regardless of whether or not the water molecules are bound to the polymers. However, the methods for determining moisture content of a dielectric materials in accord with this invention are particularly useful at low moisture levels in polymers having polar groups, i.e. where a substantial portion of the moisture content of the polymer consists of bound water.

A method for determining the moisture content of a dielectric material, in accord with this invention, comprises subjecting said material to a low frequency electrical field and determining the loss tangent or the dielectric loss factor of said material. In one embodiment of the invention the dielectric loss factor (E") of the dielectric material is measured at the frequency of maximum dielectric loss due to the presence of water.

Another method for determining the moisture content of a dielectric material, in accord with this invention, comprises subjecting said material to a step change in voltage and determining the direct current flow at a predetermined time after said step change in voltage.

For purposes of the present invention low frequency means a frequency in the range of radio waves and lower.

BRIEF DESCRIPTION OF THE DRAWINGS

FIG. 1 is a partial isometric view, party in cross-section, of a device useful for measuring dielectric properties of materials in accord with this invention.

FIG. 2 is a partial isometric view, partly in cross-section, of another device useful for measuring electrical properties of materials.

FIG. 3 is a graph illustrating electrical current as a function of time after a step voltage is applied for Nylon 66 having three different moisture levels.

FIG. 4 is a graph illustrating the change in dissipation factor or loss tangent with changes in moisture content at 20 KHz for Nylon 66.

DESCRIPTION OF THE INVENTION

Figure 5:
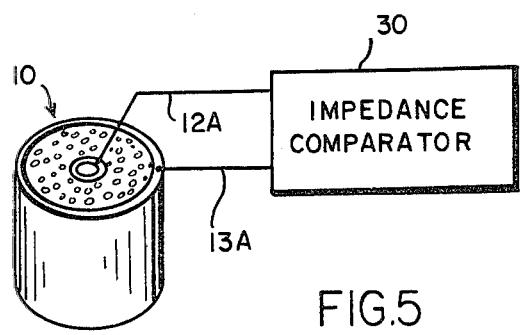
FIG. 5 is an llustration of the device of FIG. 1 connected to an impedance comparator for measuring the dielectric loss properties of materials in accord with this invention.

In accord with one embodiment of the present invention, a method for measuring moisture content of dielectric materials comprises determining the dielectric loss factor (E") of such materials at a low frequency. The measure of dielectric loss factor correlates directly with the quantity of moisture in the material.

The method can be used either with granular, powdered materials or with blocks of material. For granular or powdered materials, a device such as illustrated in FIG. 1 is preferred for measurements. For blocks of material, a device such as illustrated in FIG. 2 is preferred. Either device is calibrated for particular material by determining the loss factor (E") for a series of samples of known moisture content.

The particular frequency selected for any job may depend upon a number of variables, including, the particular dielectric material being monitored, the range of moisture level, the geometry of the electrodes, the physical state of the material (i.e. block, granule, powder), temperature, and the like. Frequencies in the range of radio waves (i.e. 10 KHz to 100 M Hz) are generally useful in the practice of this invention. However, frequencies of 100 KHz and less down to 100 Hz and less are useful for many polymers including, for instance, nylon.

The optimum or most desirable frequency can be readily selected by the average practitioner by making a few determinations of the dielectric loss index at various frequencies for several samples having different moisture contents in the range of interest. For instance, it may be that for particular situations, the frequency at which the dielectric loss is a maximum is preferred. For example, in nylon 66, for measuring moisture levels less than 1% by weight, the frequency of maximum dielectric loss is about 20,000 Hz.

Methods for determining tan δ and E" are well known in the art. Suitable measurements can be obtained from samples using the devices illustrated in FIG. 1 and FIG. 2 with a suitable bridge circuit such as a General Radio capacitance bridge (Model 716-C) or the like. Conventionally available bridge circuits may require some modification for very low frequencies, say 100 Hz or less. Such modifications are well-known and readily accomplished by the skilled artisan.

With reference to FIG. 1, the moisture content of a sample of polymer granules 15 is determined by filling device 10 with granules between inner electrode 12 and outer electrode 13. An alternating current having a preselected frequency is provided to the electrodes through leads 12A and 13A. The bottom plate 18 of the device consists of an insulating material. The tan δ and/or E" are determined and moisture content is readily determined from a calibration chart.

Device 20 illustrated in FIG. 2 is used in a similar manner for block samples. When using the device 20 it may be preferable to coat the surface of sample 25 with a layer 26 conducting grease or vapor deposited silver or gold to obtain increased sensitivity. Then plate electrodes 22 and 23 are connected to a source of alternating current by means of leads 22A and 23A. The tan δ and/or E" are determined as above and the moisture content is readily determined from a calibration chart.

In accord with another embodiment of our invention the moisture content of a dielectric material is determined by applying a D.C. step voltage across a sample of the material and measuring the electrical current after a preselected time interval. The current is directly proportional to the moisture content of the material which is determined by a calibration curve. The current is also proportional to the step voltage applied, which must be less than the breakdown voltage of the material.

Other aspects and advantages of this invention will be apparent to those skilled in the art upon consideration of the following examples which are provided to further illustrate the invention.

EXAMPLE 1

The dissipation factor of granules of nylon 66 conditioned to three different moisture levels was determined at the moisture-sensitive frequency (20,000 Hz) using a device as illustrated in FIG. 1. The particular device had the following dimensions: inside radius of outer electrode 9.916 cm., and its height 12.725 cm., outside radius of inner electrode 5.072 cm., and its height 9.66 cm. Electrical measurements were made using a capacitance bridge and current was generated using frequency generator. The three different moisture levels are plotted against their dissipation factors (tan δ) in FIG. 4.

EXAMPLE 2

Samples of nylon 66 having the following dimensions: diameter 4.996 cm, thckness 0.315 lm were prepared and conditioned to various moisture levels. The dielectric properties of the samples were determined using a device as illustrated in FIG. 2 and the other apparatus as identified in Example 1. The dielectric loss factor, E", is tabulated below.

TABLE 1

| Dielectric Properties of Nylon 66 Blocks | | |
|---|---|---|
| Frequency (Hz) | 3.45% moisture content E" | 0.26% moisture content E" |
| 0.02 | 78.4 | 0.0995 |
| 0.05 | 36.7 | 0.635 |
| 0.1 | 21.41 | 0.050 |
| 0.2 | 13.72 | 0.040 |
| 0.5 | 7.43 | 0.031 |
| 1 | 4.91 | 0.029 |
| 2 | 3.416 | 0.022 |
| 3.33 | 2.633 | 0.0192 |
| 5 | 2.172 | 0.019 |
| 10 | 1.629 | 0.020 |
| 20 | 1.286 | 0.023 |
| 100 | 0.925 | 0.033 |
| 1000 | 0.926 | 0.0556 |
| 10000 | 0.787 | 0.0756 |
| 100000 | — | 0.0692 |

EXAMPLE 3

Samples of nylon 66 were prepared as in Example 2. An electric field is applied across the electrodes and the direct current is monitored. A step increase of voltage to 260 volts is applied. The decay in current is monitored and the value 10 seconds after the step increase in voltage is determined. The results are tabulated below.

TABLE 3

| D.C. Conductivity In Nylon 66 After Step Change In Voltage | |
|---|---|
| Moisture Content of Polymer | Current, Amps After 10 seconds |
| 0.26% | $5. \times 10^{-13}$ |
| 3.45% | $3.5 \times 10^{-10}$ |

EXAMPLE 4

Three samples of nylon 66 are prepared as in Example 3 except they are conditioned to 0.9%, 0.7% and 0.5% moisture, respectively. An electric field is applied to the samples contained in the device of FIG. 2 and a step voltage is applied as in Example 3. The change in direct current with time was recorded on a oscilloscope and is illustrated in FIG. 3.

It can be seen that the current for the three moisture levels differ by a factor of about 2 each after 10 seconds.

A variety of polymers have been tested in accord with the method for measuring dielectric loss in accord with this invention. It was found that the moisture sensitivity, in general, does not vary substantially for changes in frequency near the most sensitive frequency. Thus, the order of magnitude of the most moisture-sensitive frequency for each of the polymers are tabulated below:

| polymer | frequency, Hz order of magnetude |
|---|---|
| polyamide | $\sim 10^4$ |
| poly(amide-imide) | $\sim 10^5$ |
| polyethylene terephthalat | $\sim 10^5$ |
| polycarbonate | $\sim 10^7$ |
| polymethylmethacrylate | $\sim 10^5$ |
| polyurethane (thermoplastic) | $\sim 10^3$ |

It should be noted that the loss factor is proportional to the loss tangent if the dielectric constant is the same. Since the change in the dielectric constant due to the absorbed moisture is negligible at low moisture levels the loss tangent is approximately proportional to the loss factor. Hence, either the loss tangent or the loss factor can be used in determining the moisture levels in polymers. Also, since the value of the loss tangent (tan δ) is small, the value of angle (δ) is approximately equal to the loss tangent.

An accurate, fast, and on-line measurement of the moisture level in polymers is possible if a comparative measurement technique is used. The exact value of the moisture content is not required, for example, during injection molding or extrusion; instead an indication of whether the moisture level is lower or higher than a level desired would be sufficient and perhaps more useful. By calibrating two standard values, one for the minimum and the other for the maximum acceptable moisture levels, a continuous monitoring of the polymer resins within a desired moisture level is possible. Whenever the moisture level of the resins is within the acceptable range, the dryer can be turned off. In so doing, overheating can be eliminated leading to a substantial savings in energy cost.

The sensitivity of comparative measurement depends on how precisely the transformer in the bridge could be balanced. When the arms of the impedance comparator is balanced to be equal within one part in $10^6$ (General Radio Type 16-5-A Spec.), a detector sensitivity of $2.10^{-5}$ radians in phase difference can be attained from the comparative measurement.

The type 16-5-A impedance comparator made by General Radio Company is designated to measure and indicate on meters the magnitude and phase-angle difference between two external impedances. Because no bridge-balancing operation is necessary, the measurement may be made rapidly. The comparative type of measurement is particularly suitable for industrial application because, as aforesaid, an absolute measurement is not generally necessary for processing.

With reference to FIG. 5, the impedance comparator 30 has an adjustable standard box (not shown). The adjustable standard box is nothing but a variable capacitor and a variable resistor in parallel. When an unknown sample is connected to one leg of the bridge (not shown), the capacitor and the resistor in the standard box are adjusted until the phase angle and the impedance difference meters can be brought to a null position. The phase angle difference meter is used to determine whether an unknown sample has a higher or lower moisture content than a standard sample of known moisture content.

In one example of using the comparator, the resistor and the capacitor in the standard box were adjusted so that the phase angle difference and the impedance difference readings were zero when a 0.2% moisture level sample was used as a standard sample. Then a 0.6% moisture level sample was measured to have +0.0007 radians (rad.) and a 0.1% moisture level sample had −0.00045 rad. reading.

Since the phase angle difference meter of the impedance comparator is sensitive up to $2 \times 10^{-5}$ rad., an accurate and fast comparative measurement is possible.

A sensitivity of 0.005% by weight is estimated if the response of the phase angle difference is linear between 0.1% and 0.2% moisture levels. On the other hand, a sensitivity of 0.1% is estimated assuming a linear response between 0.2% and 0.6% moisture levels.

As the sample size increases, the limitation due to noise in the measurement system becomes smaller. And, in the 3-terminal measurement, noise problems are virtually eliminated. Hence, more sensitive measurement can be achieved if the sample size increases or 3-terminal measurement is made. Also, more sensitive measurement can be made if a more sensitive phase angle difference meter is used. For example, the type 1605-AH (General Radio) has a 3-to-1 better sensitivity than the type 16-5-A (G.R.).

The loss factor reading increases exponentially as temperature increases. In on-line monitoring of the moisture level a microprocessor can be used to compensate the changes in the reading due to the temperature change. Methods for compensating for temperature change are well known to those skilled in the art and thus need not be discussed here.

The invention has been described in detail, however, it will be appreciated that those skilled in the art, upon reading this disclosure, may make modifications and improvements within the spirit and scope of the invention.

We claim:

1. A method for determining the moisture content of solid dielectric materials comprises placing a sample of said material between two electrodes, applying an alternating electric field having a frequency in the range of radio waves to said electrodes, determining the dielectric loss properties of said material, and using the dielectric loss properties to determine the moisture content.

2. The method of claim 1 wherein said material is a polymer.

3. The method of claim 2 wherein said polymer is in the form of granules.

4. The method of claim 1 wherein said frequency is the frequency of maximum dielectric loss for said material.

5. The method of claim 1 wherein said material is a nylon and said frequency is about 20,000 Hz.

6. The method of claim 1 wherein said material is a polyamide and the frequency is on the order of magnitude of about $10^4$ Hz.

7. The method of claim 1 wherein said material is a poly(amide-imide) and the frequency is on the order of magnitude of about $10^5$ Hz.

8. The method of claim 1 wherein said material is a polyethylene terephthalate and the frequency is on the order of magnitude of about $10^5$ Hz.

9. The method of claim 1 wherein said material is a polycarbonate and the frequency is on the order of magnitude of about $10^7$ Hz.

10. The method of claim 1 wherein said material is a polymethylmethacrylate and the frequency is on the order of magnitude of about $10^5$ Hz.

11. The method of claim 1 wherein said material is a thermoplastic polyurethane and the frequency is on the order of magnitude of about $10^3$ Hz.

12. The method of claim 1 wherein said material contains a substantial amount of bound water.

13. The method of claim 1 wherein said dielectric loss property is the dielectric loss factor.

14. The method of claim 1 wherein said dielectric loss property is the dielectric loss tangent.

15. A method for determining the moisture content of a solid dielectric material comprises placing a sample of said material between two electrodes, applying an alternating electric field having a frequency of about 100,000 Hz or less to said electrodes, and measuring the dielectric loss properties of said material to determine the moisture content.

16. A method for determining whether the moisture content of a sample of solid dielectric material is within an acceptable predetermined range of moisture content, said method comprising:

connecting a first standard sample of said material having a known predetermined minimum moisture content to one leg of the bridge of an impedance comparator having a phase angle difference meter and an impedance difference meter, applying an alternating electric field having a frequency in the range of radio waves to said first standard sample, and nulling the phase angle difference meter and the impedance difference meter to obtain a first set of dial readings;

connecting a second standard sample of said material having a known predetermined maximum moisture content to the leg of the bridge, applying the alternating electric field having said frequency to said second standard sample, and nulling the meters to obtain a second set of dial readings;

thus, calibrating the impedance comparator;

connecting a sample of said material having an unknown moisture content to the leg of the bridge, applying the alternating current at said frequency, and nulling the meters to obtain a third set of dial readings; and comparing the third set of dial readings with the first and second sets of dial readings to determine whether the moisture content of said sample having unknown moisture content is between the moisture content of the two standard samples.

17. A method for determining the moisture content of a dielectric material comprising placing a sample of said material between two electrodes, subjecting the material to a step voltage, determining the value of direct current in said material at a preselected time interval after said step voltage is applied, and determining the moisture content of said material using the value of the direct current at said preselected time.

18. The method of claim 17 wherein said material is a polymer.

19. The method of claim 17 wherein said step voltage is less than the breakdown voltage of the material.

* * * * *